(12) United States Patent
Izumi et al.

(10) Patent No.: US 7,976,739 B2
(45) Date of Patent: Jul. 12, 2011

(54) CHROMENE COMPOUND

(75) Inventors: Shinobu Izumi, Shunan (JP); Junji Takenaka, Shunan (JP)

(73) Assignee: Tokuyama Corporation, Shunan-shi (JP)

( * ) Notice: Subject to any disclaimer, the term of this patent is extended or adjusted under 35 U.S.C. 154(b) by 76 days.

(21) Appl. No.: 12/438,403

(22) PCT Filed: Aug. 22, 2007

(86) PCT No.: PCT/JP2007/066705
§ 371 (c)(1),
(2), (4) Date: Feb. 23, 2009

(87) PCT Pub. No.: WO2008/023828
PCT Pub. Date: Feb. 28, 2008

(65) Prior Publication Data
US 2010/0230649 A1 Sep. 16, 2010

(30) Foreign Application Priority Data

Aug. 24, 2006 (JP) ................... 2006-228042
Apr. 26, 2007 (JP) ................... 2007-117488

(51) Int. Cl.
*G02B 5/23* (2006.01)
(52) U.S. Cl. ............... 252/586; 252/582; 430/270.1; 544/111; 544/150; 546/196; 549/381; 549/382
(58) Field of Classification Search ............ 522/71; 252/582, 586; 430/270.1, 19; 549/381, 382; 524/110; 544/111, 150; 546/196
See application file for complete search history.

(56) References Cited

U.S. PATENT DOCUMENTS

| | | | |
|---|---|---|---|
| 6,506,538 B1 | 1/2003 | Breyne et al. | |
| 7,048,876 B2 | 5/2006 | Izumi et al. | |
| 7,544,315 B2 * | 6/2009 | Melzig et al. | 252/586 |
| 2002/0125463 A1 | 9/2002 | Breyne et al. | |
| 2004/0094753 A1* | 5/2004 | Izumi et al. | 252/586 |
| 2004/0220292 A1 | 11/2004 | Momoda et al. | |

FOREIGN PATENT DOCUMENTS

| | | |
|---|---|---|
| FR | 2 815 034 | 4/2002 |
| JP | 2004-500319 A | 1/2004 |
| WO | WO-00/15628 A1 | 3/2000 |
| WO | WO 02/30916 | 4/2002 |
| WO | WO-02/090342 A1 | 11/2002 |
| WO | WO-03/011967 A1 | 2/2003 |

OTHER PUBLICATIONS

Supplementary European Search Report issued Jan. 25, 2010 in corresponding European application No. EP 07806182.

* cited by examiner

*Primary Examiner* — Ling-Siu Choi
*Assistant Examiner* — Bijan Ahvazi
(74) *Attorney, Agent, or Firm* — Birch, Stewart, Kolasch & Birch, LLP

(57) ABSTRACT

A chromene compound represented by the following formula (1),

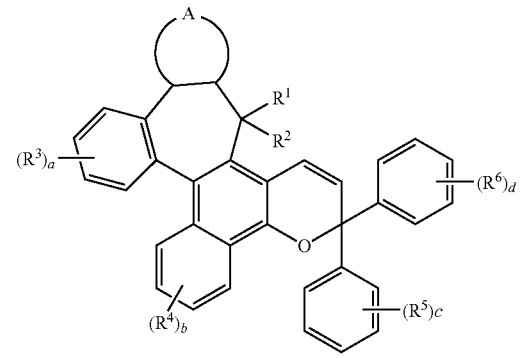

wherein,
"A" is an annulated ring, $R^1$ and $R^2$ are hydrogen atoms, hydroxyl groups or the like groups,
$R^3$, $R^4$, $R^5$ and $R^6$ are substituents such as hydroxyl groups or the like groups,
"a" and "b" are, respectively, integers of 0 to 4, and
"c" and "d" are, respectively, integers of 0 to 5.
The chromene compound is a photochromic compound developing a color of a neutral tint, and has a high color density per a unit amount.

6 Claims, No Drawings

CHROMENE COMPOUND

TECHNICAL FIELD

This invention relates to novel chromene compounds and to the use of the chromene compounds.

BACKGROUND ART

Photochromism is a reversible phenomenon of a compound which quickly changes its color when it is irradiated with light containing ultraviolet rays, such as sunlight or light of a mercury lamp and resumes its initial color when it is placed in a dark place being no longer irradiated with light. A compound having this property is called photochromic compound and is used as a material of photochromic plastic lenses.

The following properties are required for the photochromic compound used for the above application.
(1) Having a low visible coloring degree (initial color) when not irradiated with ultraviolet rays.
(2) Having a high coloring degree (color density) when irradiated with ultraviolet rays.
(3) Having a high color-developing rate which defined as an increasing rate of the color density during the period from directly after the irradiation of ultraviolet rays to the saturation of the color density.
(4) Having a high fading rate which defined as a returning rate of the color density after stopping the irradiation of ultraviolet rays.
(5) Having a good repeating durability of the reversible phenomenon.
(6) Having a good dispersibility into a monomer that is used (i.e, having an ability to dissolve into a monomer composition which is the host material after cured at a high concentration).

As for the photochromic plastic lenses, further, neutral tints such as brown and amber are preferred as color tones in the state of developing color. Naturally, therefore, what color should be developed is a very important factor for the photochromic compound.

When a color tone is adjusted by mixing a plurality of photochromic compounds together, a change in the color tone (color deviation) at the time of fading stemming from different properties of the photochromic compounds and a change in the developing color tone after aging due to a difference in the durability of the compounds are occurred. To solve the above problem, a photochromic compound which by itself develops a neutral tint is important.

The photochromic compound which by itself develops a neutral tint can be exemplified by a chromene compound of the following formula (A) (see patent document 1) and a chromene compound of the following formula (B) (see patent document 2).

(A)

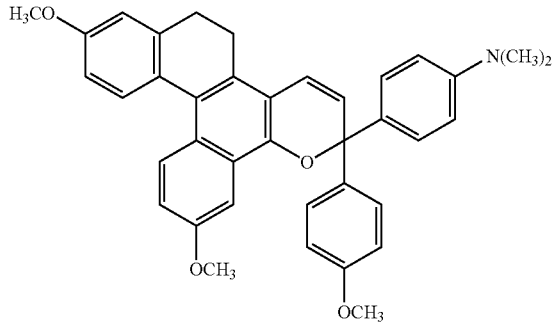

(B)

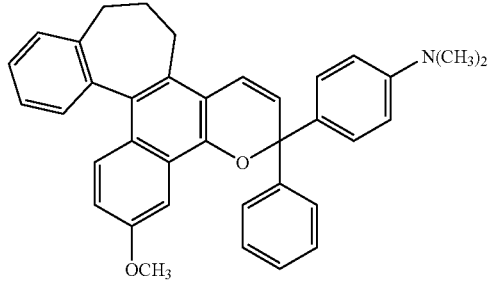

There have been obtained photochromic plastic lenses having favorable photochromic properties by curing and molding (cast-polymerizing) a curable composition obtained by dissolving the photochromic compounds in a radically polymerizable monomer relying upon the thermal radical polymerization (see patent documents 1 and 2).

The method (also called in-mass method) of producing the photochromic plastic lenses by the cast polymerization employed by the above patent documents is one of the representative methods of producing the photochromic plastic lenses imposing, however, a limitation on the polymerizable monomers that can be used for obtaining favorable photochromic properties. In recent years, a coating method free of the above limitation is drawing attention as a method of producing photochromic plastic lenses (see patent document 3). According to the coating method, a coating agent comprising a curable composition containing a photochromic compound is applied onto the surface of the lens, and the coating is cured to form a photochromic coating to thereby impart photochromic property to the lens substrate. In principle, therefore, there is no limitation on the lens substrate provided the coating can be closely adhered thereto.
Patent document 1: pamphlet of International Laid-Open WO00/15628
Patent document 2: U.S. Pat. No. 7,048,876
Patent document 3: pamphlet of International Laid-Open WO2003/011967

DISCLOSURE OF THE INVENTION

Despite of the above excellent feature, the photochromic compound used for the coating method must have photochromic properties of a level higher than the one required by the in-mass method since the photochromic property according to the coating method is imparted by using a thin layer (photochromic coating). As for the properties of the photochromic plastic lenses, the color density at the time of irradiated with the ultraviolet rays is one of the most important photochromic properties. With the coating method, however, it is not necessarily easy to obtain a high color density. The color density can be increased to some extent by increasing the concentration of the photochromic compound contained in the photochromic coating. However, the color density saturates if the concentration of the photochromic compound becomes higher than a certain degree. To obtain a high color density by the coating method, therefore, the photochromic compound itself must have a high color density. In other words, it is desired to provide a photochromic compound having a high color density per a unit amount (e.g., per mol or per a unit mass).

The photochromic compounds represented by the above formulas (A) and (B) are excellent in regard to developing neutral tints but have low color densities per a unit amount.

With the coating method, therefore, it is difficult to produce photochromic plastic lenses having a high color density by using the above compounds.

It is, therefore, an object of the present invention to provide a photochromic compound which develops a neutral tint and has a high color density per a unit amount.

According to the present invention, there is provided a chromene compound represented by the following formula (1),

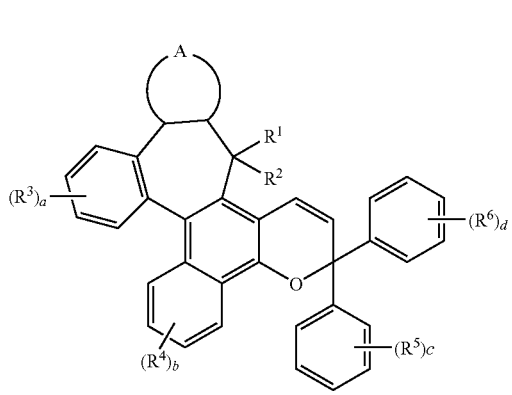

wherein,
"A" is an annulated ring,
$R^1$ and $R^2$ are, respectively, hydrogen atoms, hydroxyl groups, alkyl groups, cycloalkyl groups, alkoxy groups, aralkyl groups, aralkoxy groups or aryl groups, $R^1$ and $R^2$ may be linked to each other to form a ring, and $R^1$ and $R^2$ together may form a carbonyl group with a carbon atom to which these groups are bonded,
$R^3$, $R^4$, $R^5$ and $R^6$ are, respectively, hydroxyl groups, alkyl groups, cycloalkyl groups, alkoxy groups, aralkyl groups, aralkoxy groups, aryl groups, amino groups, cyano groups, nitro groups, halogen atoms, halogenoalkyl groups, halogenoalkoxy groups, or heterocyclic groups having a nitrogen atom as a hetero atom and being bonded through a bond at the nitrogen atom and, when $R^3$s are present in a plural number, two $R^3$s may be bonded together to form a ring,
"a" and "b" are, respectively, integers of 0 to 4, and
"c" and "d" are, respectively, integers of 0 to 5.

According to the present invention, further, there are provided:
(1) A photochromic curable composition containing the above chromene compound and a polymerizable monomer;
(2) A photochromic optical article having, as a constituent member, a high molecular molded body in which the above chromene compound is dispersed; and
(3) An optical article including, as a constituent part, an optical substrate having a surface which is at least partly coated with a high molecular film, the high molecular film having the chromene compound dispersed therein.

The chromene compound of the present invention by itself develops a neutral tint, eliminating the need of adjusting the color tone by mixing a plurality of photochromic compounds together, causing no change in the color tone at the time of color fading or no change in the color tone after aged. Further, the chromene compound features excellent light resistance permitting photochromic properties to be little deteriorated even after the photochromic reversible reaction is repeated. Owing to its high color density per a unit amount, further, the chromene compound makes it possible to obtain a photochromic lens having a high color density even when the coating method is employed.

BEST MODE FOR CARRYING OUT THE INVENTION

The chromene compound of the present invention is represented by the following formula (1),

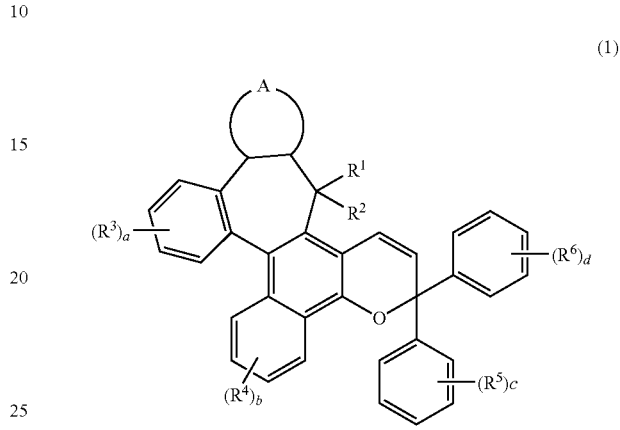

(Annulated Ring A)
In the above formula (1), "A" is an annulated ring, i.e., this ring is annulated with a 7-membered ring to which a group $R^1$ and a group $R^2$ are bonded. There is no particular limitation on the structure of the annulated ring A. From the standpoint of improving the recurring resistance, however, the annulated ring A is, preferably, (I) an aromatic hydrocarbon ring, (II) an alicyclic hydrocarbon ring, or (III) a heterocyclic ring.

A desired aromatic hydrocarbon ring (I) has 6 to 10 carbon atoms as ring members, such as benzene ring, naphthalene ring or the like ring. The aromatic hydrocarbon ring may have a substituent. As the substituent, there can be exemplified alkyl groups such as methyl group, ethyl group, propyl group, isopropyl group and butyl group; and alkoxy groups such as methoxy group, ethoxy group, propoxy group and isopropoxy group. Among these substituents, methyl group and methoxy group are particularly preferred. There is no particular limitation on the positions where the substituents are bonded to the aromatic hydrocarbon ring or on the numbers thereof.

As the alicyclic hydrocarbon ring (II), there can be exemplified the one having 4 to 12 carbon atoms as ring members, such as cyclopropane ring, cyclopentane ring, cyclohexane ring or cyclooctane ring. Like the above aromatic hydrocarbon ring, the alicyclic hydrocarbon may have a substituent. The substituents may be those exemplified above concerning the aromatic hydrocarbon ring (I). Among them, methyl group and methoxy group are particularly preferred. There is no particular limitation on the positions where the substituents are bonded to the alicyclic hydrocarbon ring or on the numbers thereof.

A preferred heterocyclic ring (III) has at least one or more hetero atoms such as oxygen, sulfur and nitrogen in the atoms constituting the ring, and has 4 to 10 atoms constituting the ring. Preferred examples of the heterocyclic ring include furan ring, thiophene ring, pyrrole ring, pyridine ring, pyrrolidine ring, piperidine ring, morpholine ring, indole ring, benzofuran ring, benzothiophene ring, quinoline ring, isoquinoline ring, indoline ring and chroman ring. When the hetero atom is a nitrogen atom and a hydrogen atom is bonded to the nitrogen atom, the hydrogen atom may be substituted by the methyl group.

Among the above annulated rings A in the chromene compounds of the present invention, the aromatic hydrocarbon ring (I) is most desired from the standpoint of improving the color density.

(Groups $R^1$ and $R^2$)

In the above formula (1), $R^1$ and $R^2$ are, respectively, hydrogen atoms, hydroxyl groups, alkyl groups, cycloalkyl groups, alkoxy groups, aralkyl groups, aralkoxy groups or aryl groups, and $R^1$ and $R^2$ together may form a ring.

Though there is no particular limitation, the preferred alkyl group is an alkyl group having, usually, 1 to 9 carbon atoms, such as methyl group, ethyl group, propyl group, isopropyl group, butyl group, s-butyl group or t-butyl group.

Though there is no particular limitation, the preferred cycloalkyl group has, usually, 3 to 12 carbon atoms, such as cyclopropyl group, cyclobutyl group, cyclopentyl group, cyclohexyl group, cycloheptyl group or cyclooctyl group.

Though there is no particular limitation, the preferred alkoxy group has, usually, 1 to 5 carbon atoms, such as methoxy group, ethoxy group, propoxy group, isopropoxy group, butoxy group, s-butoxy group, t-butoxy group, pentyloxy group or neopentyloxy group.

Among the alkoxy groups, further, there can be preferably used a substituted alkoxy group having an alkoxy group as a substituent as represented, for example, by the following general formula,

wherein
$R^a$ is methylene group, ethylene group or propylene group, and
$R^b$ is methyl group, ethyl group or propyl group.

Methoxymethoxy group, methoxyethoxy group and ethoxyethoxy group are most desired among the above substituted alkoxy groups.

Though there is no particular limitation, the preferred aralkyl group is the one having, usually, 7 to 11 carbon atoms, such as benzyl group, phenylethyl group, phenylpropyl group or phenylbutyl group.

Though there is no particular limitation, the preferred aralkoxy group is the one having, usually, 6 to 10 carbon atoms, such as phenoxy group or naphthoxy group.

Though there is no particular limitation, the preferred aryl group is an aromatic hydrocarbon group having 6 to 10 carbon atoms or an aromatic heterocyclic group having 4 to 12 carbon atoms forming a ring. Concrete examples of the aryl group include phenyl group, naphthyl group, thienyl group, furyl group, pyrrolinyl group, pyridyl group, benzothienyl group, benzofuranyl group and benzopyrrolinyl group. It is further desired to use a substituted aryl group in which one or two or more hydrogen atoms of the aryl group are substituted by the same substituents as those described above, such as alkyl groups, alkoxy groups, aralkyl groups or aralkoxy groups.

The ring formed by the linkage of the group $R^1$ and the group $R^2$ is, preferably, a ring having 3 to 10 carbon atoms forming a ring. As the above ring, there can be exemplified an aliphatic hydrocarbon ring and a hetero ring including hetero atoms such as oxygen atom, nitrogen atom and sulfur atom. The aliphatic hydrocarbon ring or the hetero ring may further have an alkyl group or alkoxy group with 1 to 5 carbon atoms as a substituent (there is no particular limitation on the number of the substituents or on the positions of substitution) and may, further, be annulated with an aromatic hydrocarbon ring such as benzene or naphthalene. Shown below are concrete examples of the ring formed by the above group $R^1$ and the group $R^2$. In the following rings, the carbon atom (spiro carbon atom) at the lowermost position and having two bonds corresponds to the carbon atom in the 7-membered ring to which the group $R^1$ and the group $R^2$ are bonded.

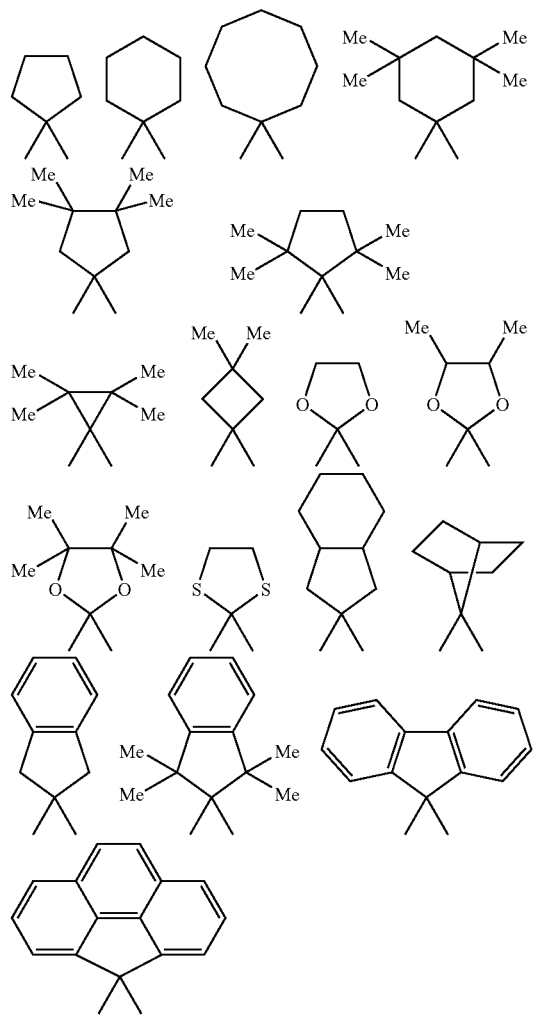

Further, the above group $R^1$ and the group $R^2$ together may form a carbonyl group with a carbon atom to which these groups are bonded. That is, the carbon atom in the carbonyl group (>C=O) is a carbon atom in the 7-membered ring, and the oxygen atom in the carbonyl group is represented by the group $R^1$ and the group $R^2$ in combination.

(Group $R^3$ to Group $R^6$)

In the above formula (1), the groups $R^3$, $R^4$, $R^5$ and $R^6$ are, respectively, hydroxyl groups, alkyl groups, cycloalkyl groups, alkoxy groups, aralkyl groups, aralkoxy groups, aryl groups, amino groups, cyano groups, nitro groups, halogen atoms, halogenoalkyl groups, halogenoalkoxy groups, or heterocyclic groups.

Here, as for the alkyl group, cycloalkyl group, alkoxy group, aralkyl group, aralkoxy group and aryl group, there can be preferably exemplified the same substituents as those described above concerning the above group $R^1$ and the group $R^2$.

The amino group is not limited to the primary amino group and may be a secondary amino group or a tertiary amino group having a substituent. Though there is no particular limitation, the substituent possessed by the amino group is typically an alkyl group or an aryl group. Preferred examples of the substituted amino group (secondary amino group or tertiary amino group) include alkylamino groups such as methylamino group and ethylamino group; dialkylamino groups such as dimethylamino group and diethylamino group; arylamino groups such as phenylamino group and the like group; and diarylamino groups such as diphenylamino group and the like group.

As the halogen atom, there can be exemplified fluorine atom, chlorine atom, bromine atom or iodine atom.

As the halogenoalkyl group, there can be exemplified the one in which one or two or more hydrogen atoms of the alkyl group shown concerning the above group $R^1$ and the group $R^2$ are substituted by fluorine atoms, chlorine atoms or bromine atoms. Among them, the one substituted with fluorine atoms, such as fluoromethyl group, difluoromethyl group or trifluoromethyl group is preferred.

As the halogenoalkoxy group, there can be exemplified the one in which one or two or more hydrogen atoms of the alkoxy group are substituted by fluorine atoms, chlorine atoms or bromine atoms. A particularly preferred halogenoalkoxy group is a fluoroalkoxy group, such as fluoromethoxy group, difluoromethoxy group or trifluoromethoxy group.

Further, the heterocyclic group has a nitrogen atom as a hetero atom, the nitrogen atom being bonded thereto as a bonding hand. The heterocyclic group is highly effective in improving the dissolution of the chromene compound in the monomer component, and is, particularly, preferred from the standpoint of enhancing the dispersibility of the chromene compound in the host material. Representative examples of the heterocyclic group include morpholino group and piperidino group. The heterocyclic group may, further, have an alkyl group such as methyl group as a substituent. As the heterocyclic group having the above substituent, there can be exemplified 2,6-dimethylmorpholino group, 2,6-dimethylpiperidino group and 2,2,6,6-tetramethylpiperidino group.

In the present invention, the above groups $R^3$, $R^4$, $R^5$ and $R^6$ are, preferably, alkyl groups having 1 to 6 carbon atoms, alkoxy groups having 1 to 5 carbon atoms, or heterocyclic groups.

(a to d)

In the above formula (1), "a", "b", "c" and "d" represent numbers of the groups $R^3$, $R^4$, $R^5$ and $R^6$, "a" and "b" being, respectively, integers of 0 to 4, and "c" and "d" being, respectively, integers of 0 to 5. From such a standpoint that the chromene compound develops a color tone of a neutral tint, "a" is desirably 0 to 2, and at least one of "b", "c" and "d" is 0 to 2. Further, when at least one of the numbers "b", "c" and "d" is 2, the two groups $R^4$ and $R^5$ or $R^6$ are bonded at the positions shown in the following formulas (4) to (6).

In the following formulas (4) to (6), the group $R^8$ and the group $R^9$ represent two groups $R^4$, the groups $R^{10}$ and the group $R^{11}$ represent two groups $R^5$, and the group $R^{12}$ and the group $R^{13}$ represent two groups $R^6$.

(4)

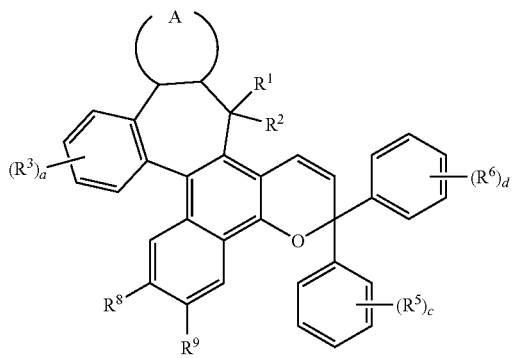

(5)

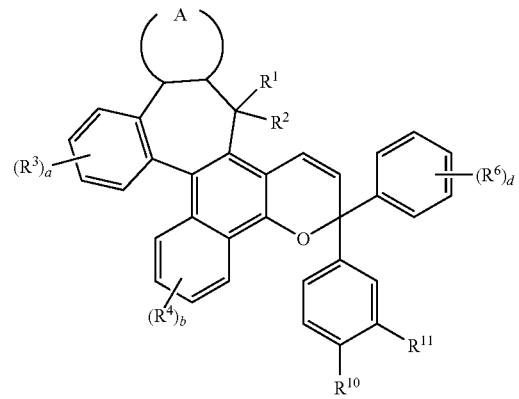

(6)

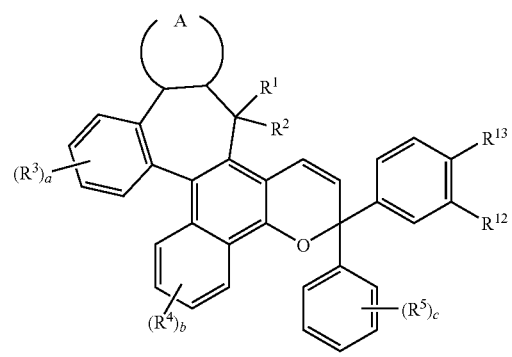

In the present invention, further, when the groups $R^4$ are present in a plural number, the plurality of groups $R^4$ may be bonded together to form a ring. In the above formula (4), for example, the group $R^8$ and the group $R^9$ may be bonded together to form a ring B shown by the following formula (7).

(7)

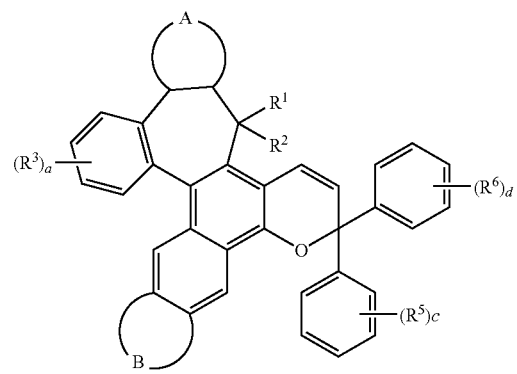

As the ring B in the above formula (7), there can be exemplified an aliphatic ring, an aromatic ring and a heterocyclic ring having 5 to 7 elements forming a ring. The ring B may have an alkyl group such as methyl group as a substituent. As the heterocyclic ring, further, there can be exemplified the one having 1 to 2 hetero atoms such as oxygen atoms, nitrogen atoms or sulfur atoms. Preferred examples of the ring B are as shown below.

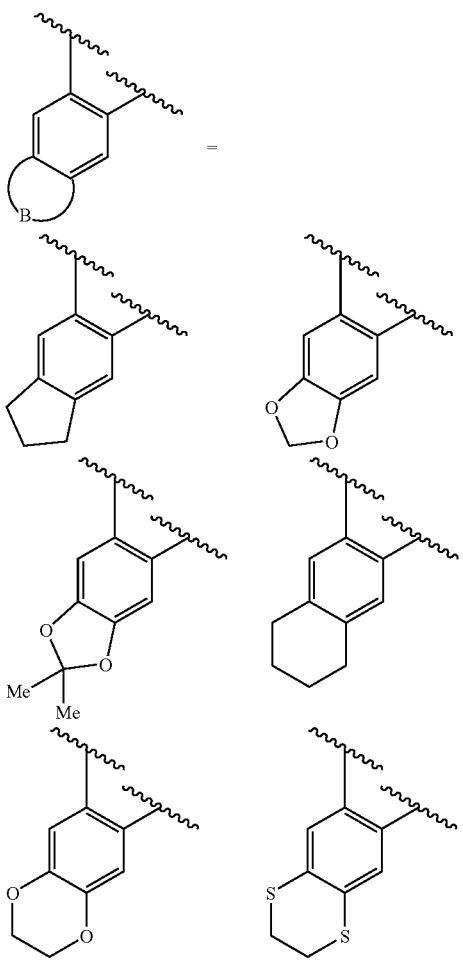

(Concrete Chromene Compounds)

In the present invention, a particularly preferred chromene compound can be represented by the following formula (2). In the formula (2), the group $R^7$ has the same meaning as the above group $R^3$, and "e" represents the number of the groups $R^7$s and is an integer of 0 to 4.

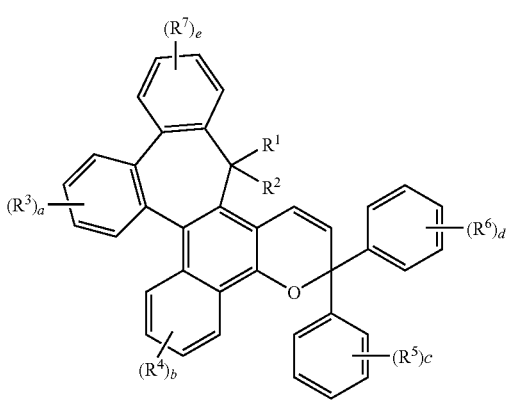

(2)

In the chromene compound represented by the above formula (2), it is desired that the group $R^4$ is bonded at a position shown in the following formula (3).

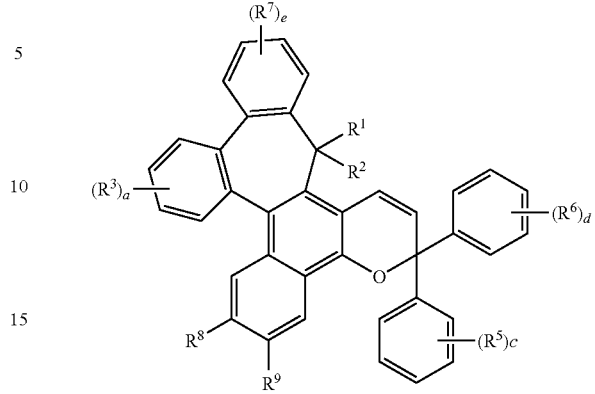

(3)

The following compounds are concrete examples of the chromene compound represented by the above formula (3).

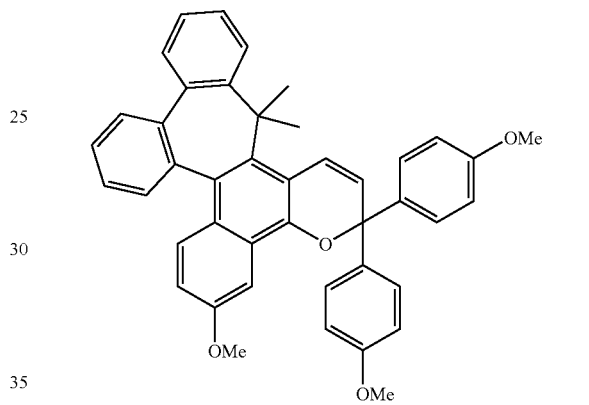

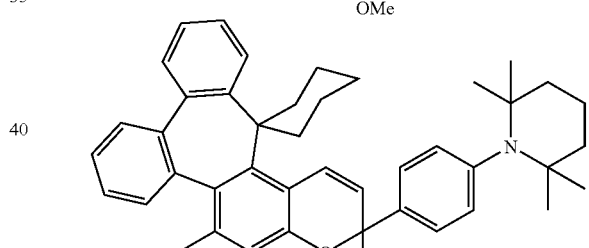

Under the conditions of normal temperature and normal pressure, in general, the chromene compound of the present invention is present as a colorless or light yellow solid or a viscous solution which can be confirmed by the following means (a) to (c).

(a) Measurement of a proton nucleus magnetic resonance spectrum ($^1$H-NMR) reveals peaks based on an aromatic proton and on a proton of an alkene near δ 5.0 to 9.0 ppm and peaks based on protons of an alkyl group and an alkylene group near δ 1.0 to 4.0 ppm. Further, the number of protons of the bonding groups can be learned from the comparison of the spectral intensities with each other.

(b) The compositions of the corresponding products can be determined by the elementary analysis.

(c) Measurement of a $^{13}$C-nuclear magnetic resonance spectrum ($^{13}$C-NMR) reveals a peak based on the carbon atom of an aromatic hydrocarbon group near δ 110 to 160 ppm, peaks based on the carbon atoms of an alkene and an alkyne near δ 80 to 140 ppm, and peaks based on the carbon atoms of an alkyl group and an alkylene group near δ 20 to 80 ppm.

(Preparation of Chromene Compounds)

The chromene compound of the present invention represented by the formula (1) can be prepared, for example, by the following method.

That is, a naphthol derivative represented by the following formula (i),

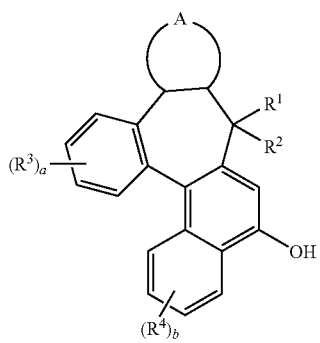

(i)

wherein the annulated ring A, $R^1$ to $R^4$, "a" and "b" are as defined in the above formula (1), which is a starting material is reacted with a propargyl alcohol derivative in the presence of an acid catalyst to prepare the chromene compound of the present invention.

The naphthol derivative represented by the above formula (i) can be produced through the following three steps of reaction (in the following reaction steps, the annulated ring A, $R^1$ to $R^4$, and a and b are all as defined in the formula (1)).

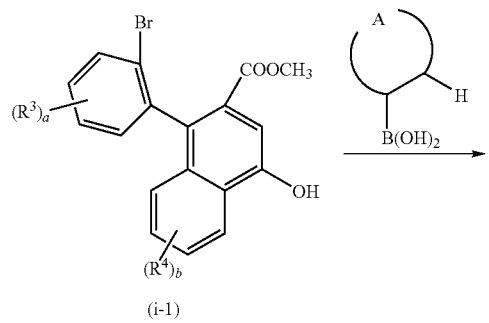

(i-1)

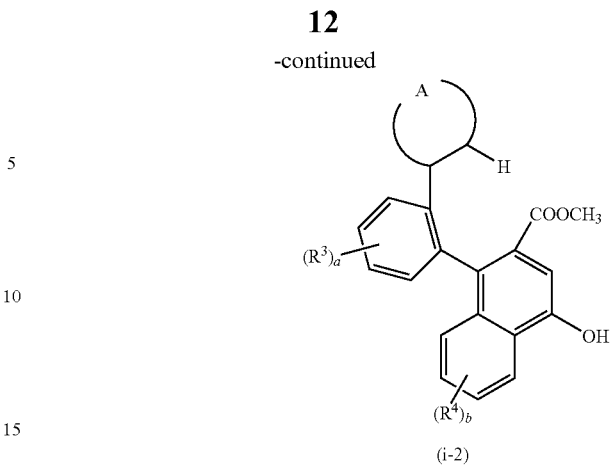

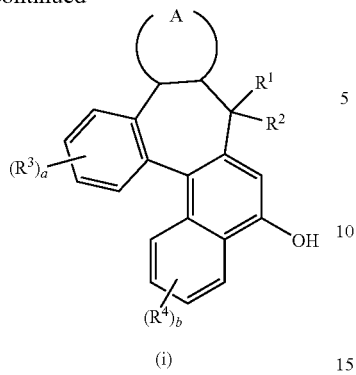

(i)

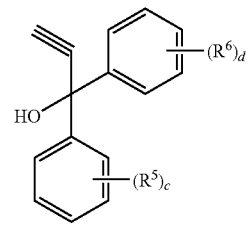

(ii)

wherein $R^5$, $R^6$, "c" and "d" are as defined in the above formula (1).

The propargyl alcohol derivative represented by the above formula (ii) can be synthesized by, for example, reacting a ketone derivative corresponding to the above formula (ii) with a metal acetylene compound such as lithium acetylide.

The naphthol derivative represented by the formula (i) is reacted with the propargyl alcohol derivative represented by the formula (ii) in the presence of an acid catalyst. Here, the reaction ratio of these two kinds of compounds is, usually, selected from a range of 1:10 to 10:1 (mol ratio).

Further, sulfuric acid, benzenesulfonic acid, p-toluenesulfonic acid or acidic alumina is used as the acid catalyst in an amount in a range of 0.1 to 10 parts by mass per a total of 100 parts by mass of the naphthol derivative and the propargyl alcohol derivative. The reaction temperature is, preferably, 0 to 200° C., and a non-protonic organic solvent such as N-methylpyrrolidone, dimethylformamide, tetrahydrofuran, benzene or toluene is used as the solvent.

There is no particular limitation on the method of refining the product obtained by the reaction. For example, a silica gel column refining is conducted followed by recrystallization to refine the product.

(Properties and Use of the Chromene Compounds)

The thus obtained chromene compound of the present invention dissolves well in a general organic solvent such as toluene, chloroform or tetrahydrofuran. When the chromene compound of the invention is dissolved in the above solvent, the solution thereof is, usually, colorless and transparent, and exhibits a good photochromic action of quickly developing a color when it is irradiated with sunlight or ultraviolet rays and reversibly and quickly returning to its initial colorless state when light is shut off.

The chromene compound of the present invention can be applied to the use of optical articles such as plastic lenses. For example, the chromene compound is mixed into a polymerizable monomer that will be described later to prepare a photochromic curable composition for producing a photochromic plastic lens based on the coating method or the in-mass method. In particular, the chromene compound of the invention by itself develops a color of a neutral tint without the need of using other photochromic compounds and, further, features a high color density per a unit amount. Therefore, the photochromic plastic lens prepared by the coating method, too, exhibits good photochromic properties.

When the photochromic plastic lens is to be prepared by the coating method by using the chromene compound of the present invention, the preparation method can be conducted in the same manner as that of the conventional coating method. For example, the photochromic coating agent is prepared according to a method described in the patent document 3 mentioned above, is applied onto the lens surface and is cured to thereby produce a photochromic plastic lens.

The photochromic coating agent can be prepared by dissolving the photochromic compound in a monomer compo- Through the first step of the reaction, a naphthol derivative (i-1) is reacted with a boric acid derivative having a ring A to synthesize a naphthol derivative (i-2). The reaction is conducted in the presence of a palladium catalyst and a base. A tetrakistriphenylphosphine palladium is used as the palladium catalyst and a sodium carbonate or a potassium carbonate is used as the base. The reaction ratio of the naphthol derivative (i-1) with the boric acid derivative is selected from a range of 1:1 to 1:4 (mol ratio). Further, the palladium catalyst is added in an amount, preferably, in a range of 0.1 to 5.0 mol % per the naphthol derivative (i-1) and the base is added in an amount, preferably, in a range of 1 to 3 mol times per the naphthol derivative (i-1). The reaction temperature is, preferably, 40 to 100° C., and tetrahydrofuran, dimethoxyethane or toluene is used as the solvent.

In the second step of the reaction, the naphthol derivative (i-2) obtained through the first step of reaction is reacted with the Grignard reagent to synthesize a naphthol derivative (i-3). The reaction ratio of the naphthol derivative (i-2) with the Grignard reagent in this step of reaction is selected from a range of 1:2 to 1:10 (mol ratio). The reaction temperature is, preferably, −78 to 0° C., and tetrahydrofuran, diethyl ether, dibutyl ether or toluene is used as the solvent.

In the third step of the reaction, the naphthol derivative (i-3) obtained through the second step is reacted in the presence of an acid catalyst to synthesize the desired naphthol derivative (i).

Sulfuric acid, benzenesulfonic acid or p-toluenesulfonic acid is used as the acid catalyst in the reaction. The amount of the acid catalyst is used is selected from a range of 4 to 10 mol times per the naphthol derivative (i-3). The reaction temperature is preferably, 70 to 140° C., and tetrahydrofurane, benzene, toluene, methyl ethyl ketone, methyl isobutyl ketone, propanol or butanol is used as the solvent.

The naphthol derivative (i) obtained through the above steps is isolated, refined, and is put to the reaction with the propargyl alcohol derivative. The refining method, in this case, preferably, comprises conducting a silica gel column refining followed by recrystallization.

The propargyl alcohol derivative to be reacted with the above naphthol derivative is represented by the following formula (ii).

sition which comprises a radically polymerizable monomer (also called silyl monomer) having a silanol group or a hydrolyzing group which forms the silanol group upon the hydrolysis and an ordinary radically polymerizable monomer containing neither the silanol nor the hydrolyzing group. There is no particular limitation on the amount of the radically polymerizable monomers (silyl monomer and the ordinary radically polymerizable monomer) used in the coating agent. Preferably, however, the radically polymerizable monomers are used in an amount of 20 to 90% by mass and, particularly, 40 to 80% by mass based on the total mass of the whole coating agent. Further, the photochromic compound is blended in an amount in a range of 0.01 to 20% by mass, preferably, 0.05 to 15% by mass and, more preferably, 0.1 to 10% by mass based on the total mass of the whole coating agent. If the photochromic compound is blended in an amount of not larger than 0.01% by mass, the color density often becomes low. If the amount is not smaller than 20% by mass, on the other hand, the photochromic compound fails to dissolve in the polymerizable monomers to a sufficient degree, and becomes uneven often developing irregular color density.

Described below are examples of the silyl monomer used for the preparation of the photochromic coating agent.
γ-methacryloyloxypropyltrimethoxysilane,
γ-methacryloyloxypropyltriethoxysilane,
γ-methacryloyloxypropylmethyldimethoxysilane,
(3-acryloyloxypropyl)dimethylmethoxysilane,
(3-acryloyloxypropyl)methyldimethoxysilane,
(3-acryloyloxypropyl)trimethoxysilane,
(methacryloyloxymethyl)dimethylethoxysilane,
methacryloyloxymethyltriethoxysilane,
methacryloyloxymethyltrimethoxysilane,
methacryloyloxypropyldimethylethoxysilane, and
methacryloyloxypropyldimethylmethoxysilane.

Though there is no particular limitation on the amount of the silyl monomer that is used, it is desired that the amount of use thereof is 0.5 to 20% by mass and, particularly, 1 to 10% by mass based on the total mass of the whole coating agent.

Described below are examples of the ordinary radically polymerizable monomer containing neither the silyl group nor the hydrolyzing group.
trimethylolpropanetrimethacrylate,
trimethylolpropanetriacrylate,
tetramethylolmethanetrimethacrylate,
tetramethylolmethanetriacrylate,
trimethylolpropanetriethylene glycol triacrylate,
pentaerythritoltetramethacrylate,
dipentaerythritolhexaacrylate,
urethane oligomer tetraacrylate,
urethane oligomer hexamethacrylate,
urethane oligomer hexaacrylate,
polyester oligomer hexaacrylate,
diethylene glycol dimethacrylate,
triethylene glycol dimethacrylate,
tetraethylene glycol dimethacrylate,
tripropylene glycol dimethacrylate,
bisphenol A dimethacrylate,
2,2-bis(4-methacryloyloxyethoxyphenyl)propane, glycidyl methacrylate,
2,2-bis(4-acryloyloxypolyethylene glycol phenyl)propane having an average molecular weight of 776, and
methyl ether polyethylene glycol methacrylate having an average molecular weight of 475.

In addition to the above radically polymerizable monomers, it is also allowable to use in combination a radically polymerizable monomer having a maleimide group, such as 4,4'-diphenylmethanebismaleimide, bis(3-ethyl-5-methyl-4-maleimidephenyl)methane, 2,2-bis[4-(4-maleimidephenoxy)phenyl]propane, m-maleimidebenzoyl-N-hydroxysuccinimide ester, or succinimidyl-4-(N-maleimidemethyl)cyclohexane-1-carboxylat.

As the photochromic compound, the above-mentioned chromene compound of the present invention can be used. The chromene compound of the present invention has a feature in that the chromene compound by itself develops a color of a neutral tint without the need of using other photochromic compounds in combination and, further, has a high color density per a unit amount. When the chromene compound of the invention is used for the photochromic lens, it is allowable to use any other photochromic compounds in combination to obtain a desired color tone, as a matter of course.

As the photochromic compounds that can be used in combination with the chromene compound of the present invention, there can be used known photochromic compounds, such as naphthopyran compound, chromene compound, spirooxazine compound, spiropyran compound and fulgimide compound. Any of these other photochromic compounds may be used alone in combination with the chromene compound of the present invention, or two or more kinds of them may be used in combination. Described below are concrete examples of the photochromic compounds.

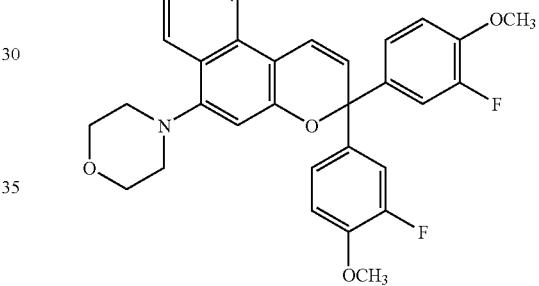

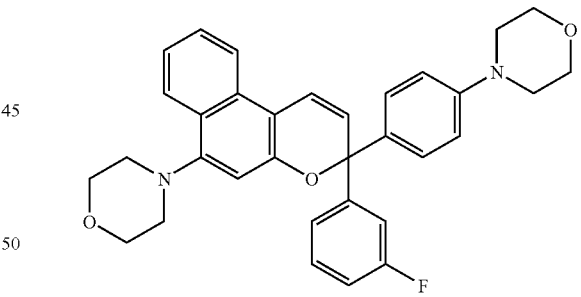

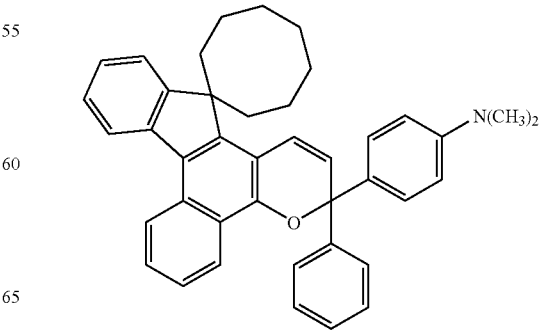

-continued

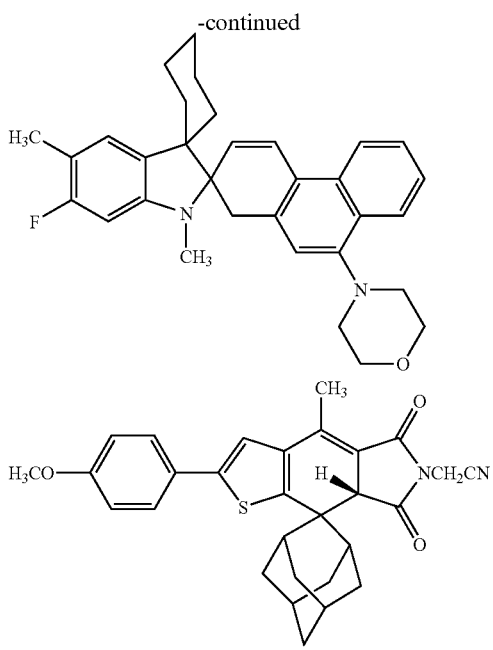

A radical polymerization initiator is, usually, added to the above photochromic coating agent. As the radical polymerization initiator, a photopolymerization initiator and/or a thermal polymerization initiator (chemical polymerization initiator) are used. The amount of the radical polymerization initiator that is used may differ depending upon the polymerization conditions, kind of the initiator, and kind and composition of the radically polymerizable monomers, and cannot be absolutely determined but is desirably in a range of 0.01 to 10% by mass based on the total mass of the whole coating agents.

Described below are examples of the polymerization initiator that can be favorably used.

Photopolymerization Initiators:
benzoin,
benzoinmethyl ether,
benzoinbutyl ether,
benzophenol,
acetophenone 4,4'-dichlorobenzophenone,
diethoxyacetophenone,
2-hydroxy-2-methyl-1-phenylpropane-1-one,
benzylmethylketal,
1-(4-isopropylphenyl)-2-hydroxy-2-methylpropane-1-one,
1-hydroxycyclohexylphenylketone,
2-isopropylthioxanthone,
bis(2,6-dimethoxybenzoyl)-2,4,4-trimethyl-pentylphosphinoxide,
bis(2,4,6-trimethylbenzoyl)-phenylphosphinoxide,
2,4,6-trimethylbenzoyldiphenylphosphinoxide, and
2-benzyl-2-dimethylamino-1-(4-morpholinophenyl)-butanone-1.

Thermal Polymerization Initiators:
diacyl peroxides such as benzoyl peroxide, p-chlorobenzoyl peroxide, decanoyl peroxide, lauroyl peroxide, and acetyl peroxide;
peroxy esters such as t-butylperoxy-2-ethylhexanoate, t-butylperoxydicarbonate, cumylperoxyneodecanoate, and t-butylperoxybenzoate;
percarbonates such as diisopropylperoxydicarbonate, di-2-ethylhexylperoxydicarbonate and di-sec-butyloxycarbonate; and
azo compounds such as 2,2'-azobisisobutylonitrile, 2,2'-azobis(4-dimethylvaleronitrile), 2,2'-azobis(2-methylbutylonitrile) and 1,1'-azobis(cyclohexane-1-carbonitrile).

To the above photochromic coating agents may be further added an amine compound such as triethanolamine, a silane coupling agent having a silanol group or a group that forms the silanol group upon the hydrolysis, such as γ-aminopropyltriethoxysilane (different from the above-mentioned silyl monomer with respect to having no polymerizable group), as well as such additives as antioxidant, radical-trapping agent, ultraviolet ray stabilizer, ultraviolet ray absorber, parting agent, anti-tinting agent, antistatic agent, fluorescent dye, dye, pigment, perfume and plasticizer to improve close adhesion, to improve light resistance of the photochromic compound, to improve the rate of developing color, to improve the fading rate and to improve the formability. It is, further, very desired to add a polymerization initiator to cure the photochromic coating agent. Known compounds can be added as additives without limitation There is no particular limitation on the method of applying the photochromic coating agent containing the chromene compound of the invention onto the lens substrate, and a known coating method can be used without limitation. Concretely, the composition can be applied by such a method as spin coating, spray coating, dip coating or dip-spin coating. There is no particular limitation on the thickness of the coating agent layer (thickness of the coating after cured) applied by the above method. Here, the lens substrate may have been treated for its surface in advance with an alkaline solution or with a plasma. Moreover, a primer may have been applied onto the surface of the lens substrate to improve close adhesion between the coating and the lens substrate (in combination with the above surface treatment or without effecting the above surface treatment).

There is no particular limitation on the method of curing the photochromic coating agent applied onto the lens substrate, and a known polymerization method may be employed depending upon the kind of the radically polymerizable monomer that is used. The polymerization can be started by such means as using a radical polymerization initiator such as various peroxides or azo compounds, irradiating ultraviolet rays, α-rays, β-rays or γ-rays, or using both of them. A particularly preferred polymerization method is to cure the curable composition of the invention blended with the above photopolymerization initiator by the irradiation with ultraviolet rays and to, further, heat the curable composition to complete the polymerization.

The photochromic plastic lens produced by the coating method using the above chromene compound of the present invention has a feature of developing a color of a neutral tint maintaining a high color density, permitting little deviation in the color that is developed and the color that is fading, and without permitting a change in the color tone that is developed even after used for extended periods of time.

As a matter of course, however, the chromene compound of the present invention is not limited for its use to the photochromic lens by the coating method only but also similarly exhibits photochromic properties in high molecular solid matrixes, too. The high molecular solid matrixes to which the invention is concerned may be those in which the chromene compound of the invention disperses homogeneously. Optically preferred examples include thermoplastic resins such as methyl polyacrylate, ethyl polyacrylate, methyl polymethacrylate, ethyl polymethacrylate, polystyrene, polyacrylonitrile, polyvinyl alcohol, polyacrylamide, poly(2-hydroxyethyl methacrylate), polydimethylsiloxane, and polycarbonate.

As the other high molecular solid matrixes, there can be exemplified thermosetting resins obtained by polymerizing the following radically polymerizable polyfunctional monomers.
Polyvalent Acrylic Acids and Polyvalent Methacrylic Acid Ester Compounds:
ethylene glycol diacrylate,
diethylene glycol dimethacrylate,
triethylene glycol dimethacrylate,
tetraethylene glycol dimethacrylate,
ethylene glycol bisglycidyl methacrylate,
bisphenol A dimethacrylate,
2,2-bis(4-methacryloyloxyethoxyphenyl)propane,
2,2-bis(3,5-dibromo-4-methacryloyloxyethoxyphenyl) propane, etc.
Polyvalent Allyl Compounds:
diallyl phthalate,
diallyl terephthalate,
diallyl isophthalate,
diallyl tartarate,
epoxydiallyl succinate,
diallyl fumarate,
diallyl chloroendoate,
diallyl hexaphthalate,
diallyl carbonate,
allyl diglycol carbonate,
trimethylolpropanetriallyl carbonate, etc.
Polyvalent Thioacrylic Acids and Polyvalent Thiomethacrylic Acid Ester Compounds:
1,2-bis(methacryloylthio)ethane,
bis(2-acryloylthioethyl)ether,
1,4-bis(methacryloylthiomethyl)benzene, etc.
Acrylic Acid Ester Compounds and Methacrylic Acid Ester Compounds:
glycidyl acrylate,
glycidyl methacrylate,
β-methylglycidyl methacrylate,
bisphenol A-monoglycidyl ether methacrylate,
4-glycidyloxy methacrylate,
3-(glycidyl-2-oxyethoxy)-2-hydroxypropyl methacrylate,
3-(glycidyloxy-1-isopropyloxy)-2-hydroxypropyl acrylate,
3-(glycidyloxy-2-hydroxypropyloxy)-2-hydroxypropyl acrylate, etc.
Other Radically Polymerizable Polyvalent Monomers:
divinylbenzene, etc.
Further, the copolymers obtained by copolymerizing the above polyfunctional monomers with monofunctional monomers, too, can be used as the high molecular solid matrixes. Exemplified below are the monofunctional monomers.
Unsaturated Carboxylic Acid:
acrylic acid, methacrylic acid, maleic anhydride, etc.
(Meth)Acrylic Acid Esters:
methyl acrylate, ethyl methacrylate, benzyl methacrylate, phenyl methacrylate, 2-hydroxyethyl methacrylate, etc.
Fumaric Acid Esters:
diethyl fumarate, diphenyl fumarate, etc.
Thio(Meth)Acrylic Acid Esters:
methyl thioacrylate, benzyl thioacrylate, benzyl thiomethacrylate, etc.
Vinyl Compounds:
Styrene, chlorostyrene, methylstyrene, vinyl naphthalene, α-methylstyrene dimer, bromostyrene, etc.
The cromene compound of the present invention exhibits photochromic properties in the above-mentioned high molecular solid matrixes, too. In obtaining the above-mentioned high molecular solid matrix by polymerization, therefore, there can be employed the in-mass method of evenly dispersing the chromene compound in the high molecular solid matrix, or a method of kneading the thermoplastic resin and the chromene compound together in a molten state so that the chromene compound is dispersed in the resin.

The high molecular molded body obtained by dispersing the chromene compound of the invention in the high molecular solid matrix can be used as a member for constituting the photochromic optical articles.

The chromene compound of the present invention can also be dispersed in the resin by dyeing the surfaces of the thermoplastic resin or the thermosetting resin with the chromene compound to thereby impart the photochromic properties to various materials.

Moreover, the chromene compound of the present invention can be applied to the uses other than the photochromic lenses; i.e., the chromene compound of the invention can be used as various memory materials such as memory materials to substitute for silver salt photosensitive materials, copying materials, photosensitive materials for printing, memory materials for cathode-ray tubes, photosensitive materials for laser, and photosensitive materials for holography. The photochromic materials using the chromene compound of the invention can also be used as a photochromic lens substrate, optical filter material, display material, actinometer, and ornamental material.

EXAMPLES

The invention will be described below in further detail by way of Examples to which only, however, the invention is in no way limited.

Example 1

The following naphthol derivative and propargyl alcohol derivative were provided.
Naphthol Derivative:

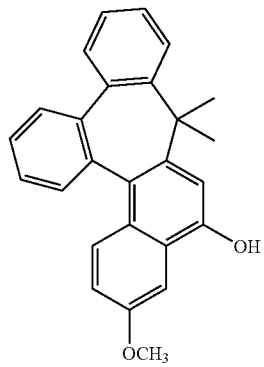

Propargyl Alcohol Derivative:

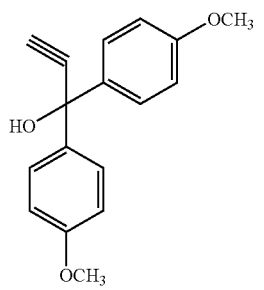

7.3 Grams (20 mmols) of the above naphthol derivative and 5.9 g (22 mmols) of the propargyl alcohol derivative were dissolved in 400 ml of toluene, and to which was further added 0.15 g of p-toluenesulfonic acid, and the mixture thereof was stirred at a refluxing temperature for 30 minutes. After the reaction, the solvent was removed, and the reaction product was refined by chromatography on silica gel to obtain 3.5 g of a white powdery product.

The product was elementary analyzed as follows:
C, 83.65%
H, 5.91%
O: 10.44%

The analytical values were in good agreement with the calculated values (C, 83.74%, H, 5.88%, O: 10.38%) of $C_{43}H_{36}O_4$.

The proton nucleus magnetic spectrum of the above product revealed a peak of 15H due to the alkylene group near δ 1.0 to 4.0 ppm, and peaks of 21H due to the aromatic proton and the proton of alkene near δ 5.2 to δ 10.0 ppm.

Further, the $^{13}C$-nuclear magnetic resonance spectrum revealed a peak due to carbon of the aromatic ring near δ 110 to 160 ppm, a peak due to carbon of alkene near δ 80 to 140 ppm, and a peak due to carbon of alkyl near δ 20 to 60 ppm.

From the above results, it was confirmed that the isolated product was a compound represented by the following structural formula,

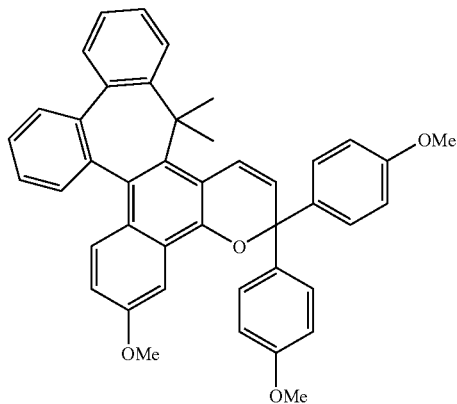

Examples 2 to 21

Chromene compounds shown in Table 1 to Table 5 were synthesized in the same manner as in Example 1.

TABLE 1

| | Starting materials | |
|---|---|---|
| Ex. No. | Naphthol derivative | Propargyl alcohol |
| 2 | ![structure] | ![structure] |
| 3 | ![structure] | ![structure] |

TABLE 1-continued
| 4 | 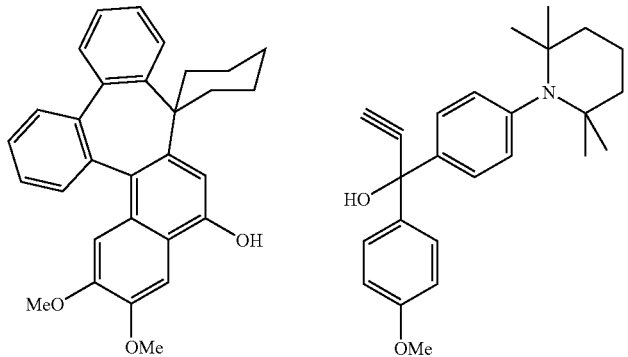 | |
| 5 | | |
| Ex. No. | Product | Yield (%) |
|---|---|---|
| 2 | 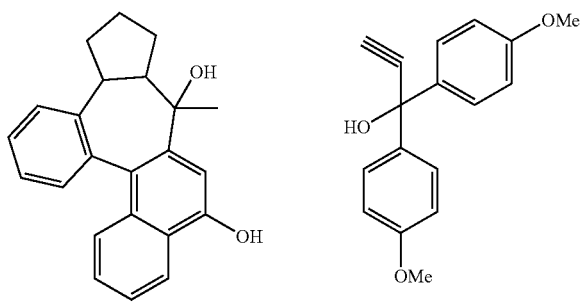 | 19 |
| 3 | 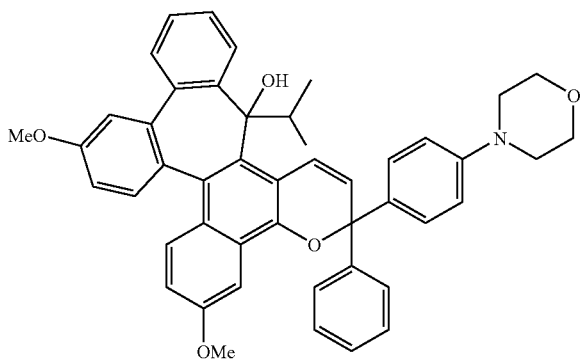 | 17 |
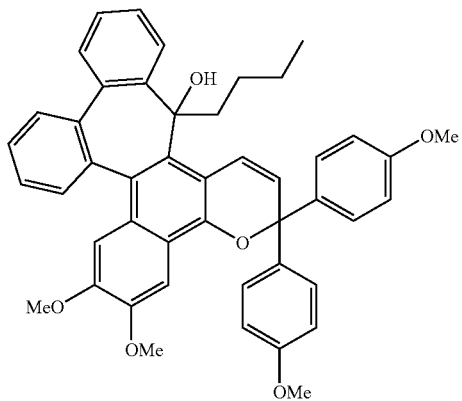

TABLE 1-continued
4 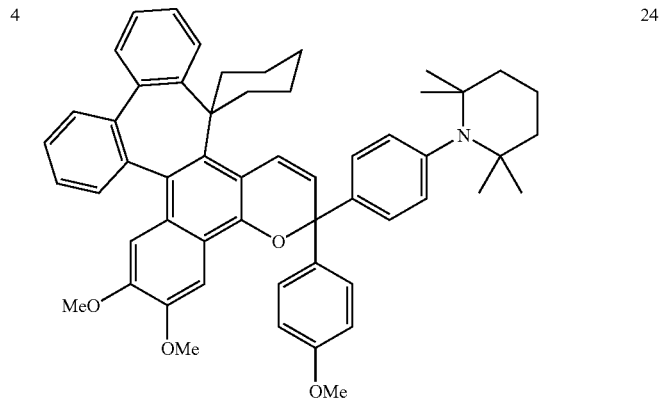 24
5 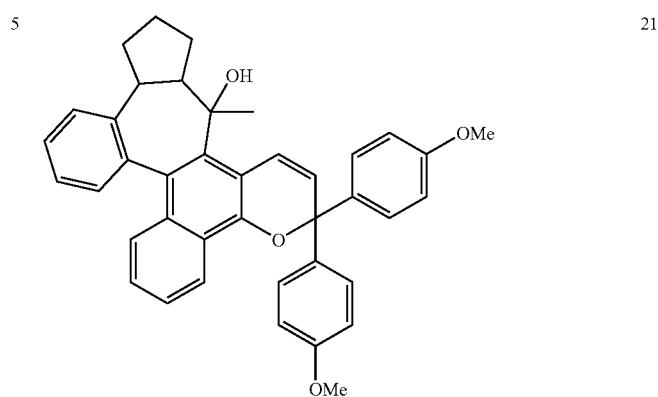 21
TABLE 2
| | Starting materials | |
|---|---|---|
| Ex. No. | Naphthol derivative | Propargyl alcohol |
| 6 | 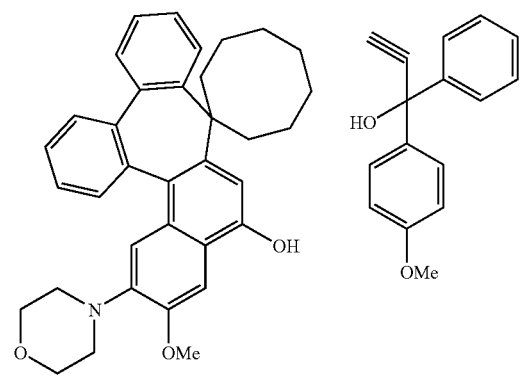 | |

TABLE 2-continued
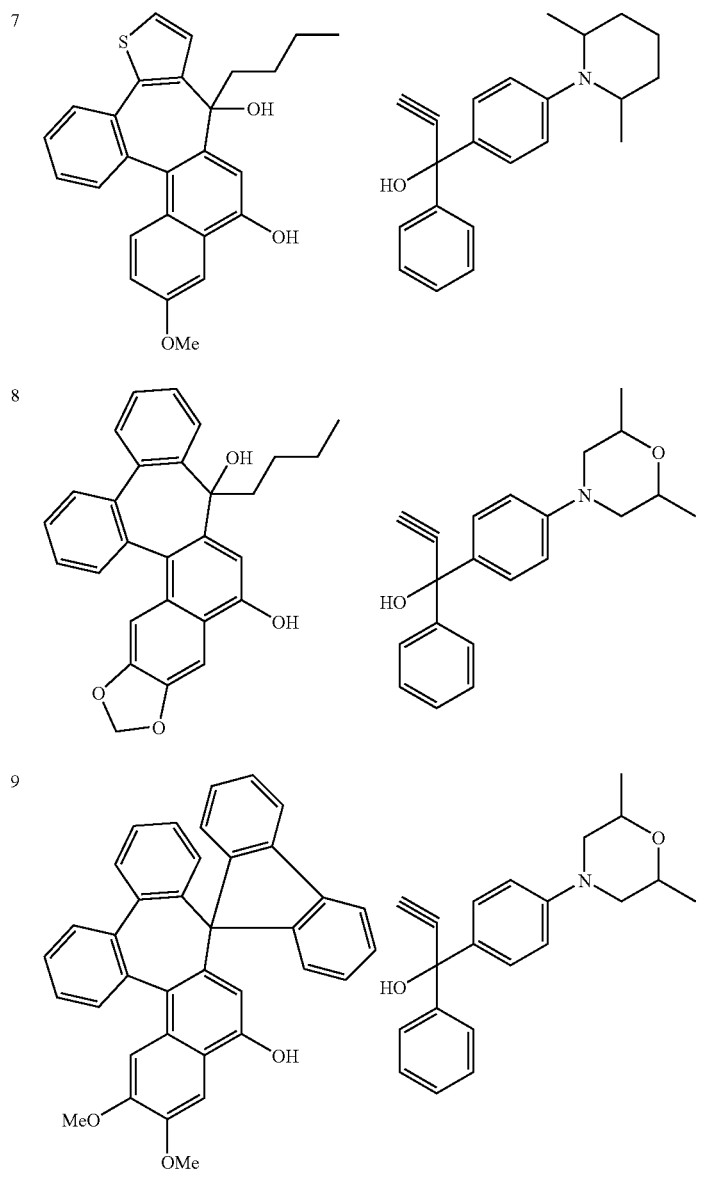
| Ex. No. | Product | Yield (%) |
|---|---|---|
| 6 | | 16 |
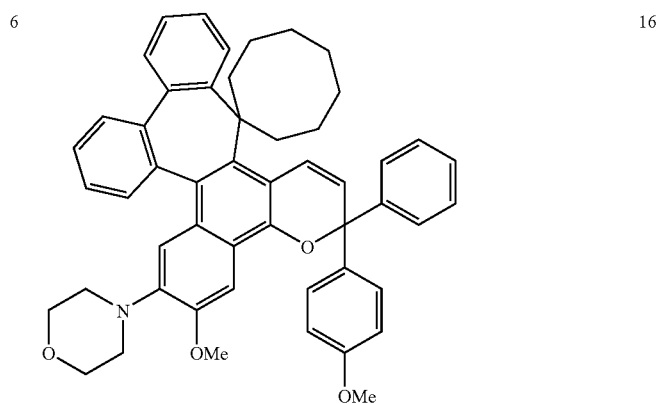

TABLE 2-continued
| 7 | 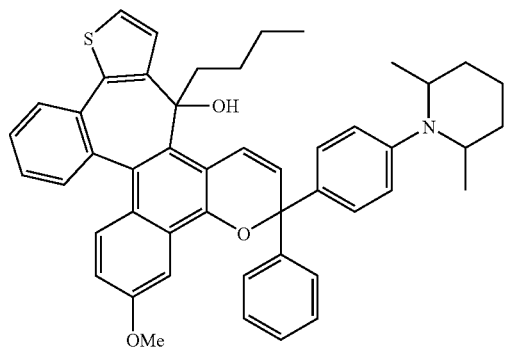 | 18 |
| --- | --- | --- |
| 8 | 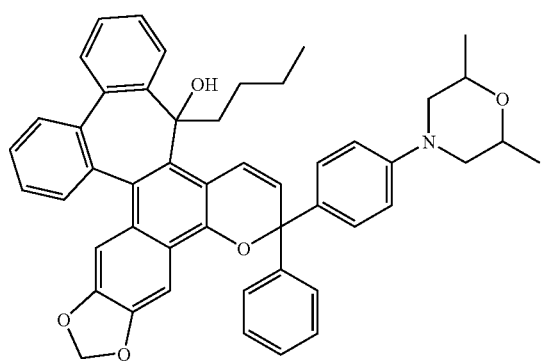 | 16 |
| 9 | 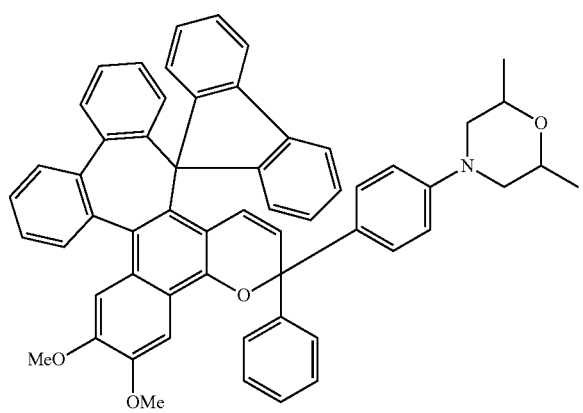 | 24 |

TABLE 3
| Ex. No. | Starting materials | |
|---|---|---|
| | Naphthol derivative | Propargyl alcohol |
| 10 | 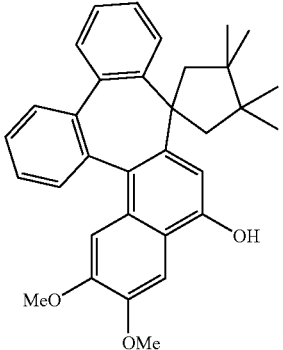 | 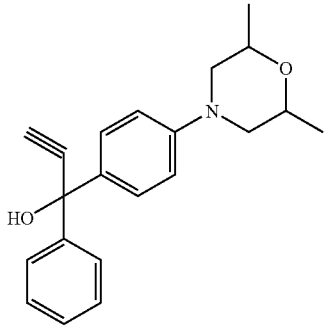 |
| 11 | 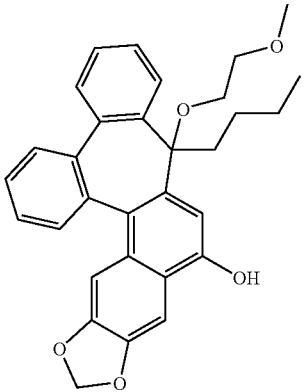 | 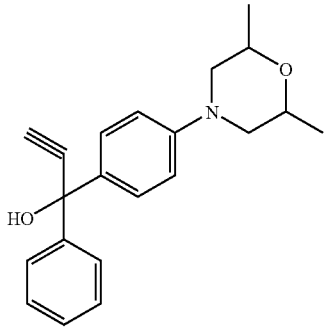 |
| 12 | 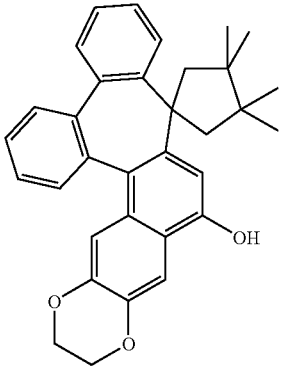 | 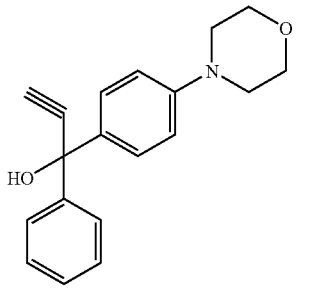 |
| 13 | 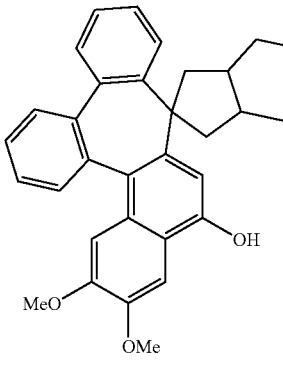 | 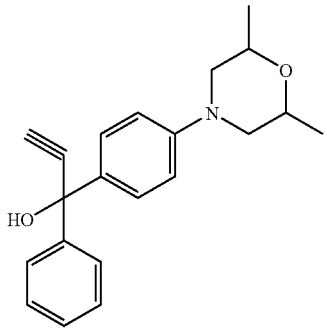 |

TABLE 3-continued
| Ex. No. | Product | Yield (%) |
|---|---|---|
| 10 | 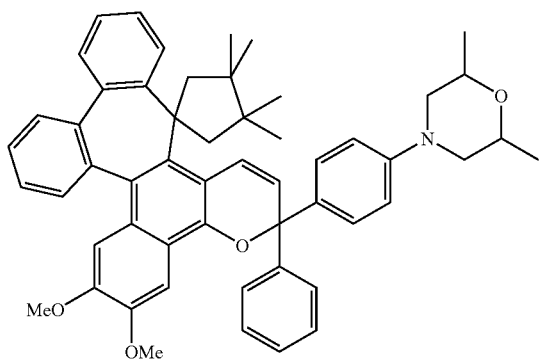 | 22 |
| 11 | 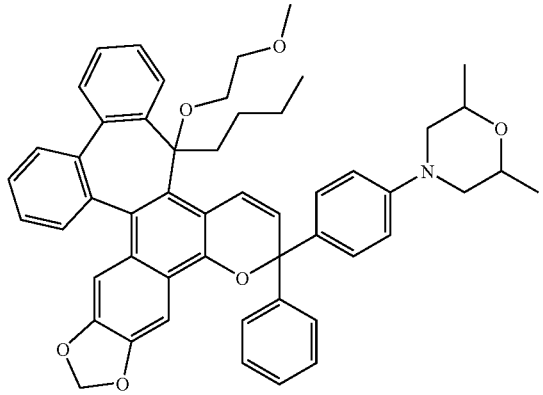 | 19 |
| 12 | 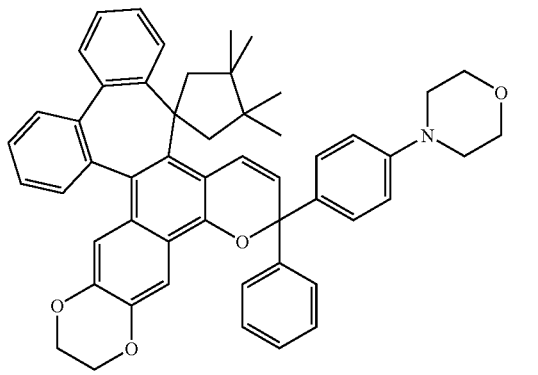 | 23 |
| 13 | 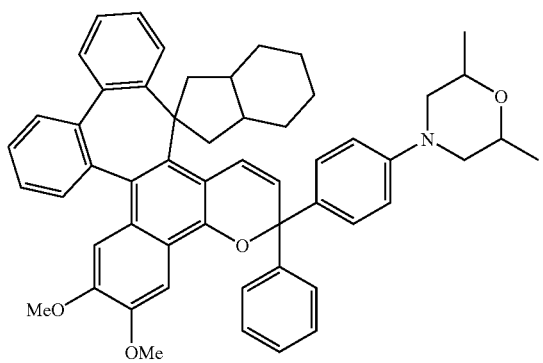 | 29 |

TABLE 4

| | Starting materials | |
|---|---|---|
| Ex. No. | Naphthol derivative | Propargyl alcohol |
| 14 | | |
| 15 | | |
| 16 | | |
| 17 | | |

TABLE 4-continued

| Ex. No. | Product | Yield (%) |
|---|---|---|
| 14 | | 33 |
| 15 | | 26 |
| 16 | | 15 |
| 17 | | 13 |

TABLE 5

| | Starting materials | |
|---|---|---|
| Ex. No. | Naphthol derivative | Propargyl alcohol |
| 18 | | |
| 19 | | |
| 20 | | |
| 21 | | |

TABLE 5-continued

| Ex. No. | Product | Yield (%) |
|---|---|---|
| 18 | | 21 |
| 19 | | 23 |
| 20 | | 21 |
| 21 | | 29 |

The obtained products were analyzed for their structures relying on the same means for confirming the structure as that of Example 1, and were confirmed to be the compounds represented by the structural formulas shown in Tables. Tables 6 and 7 show the elementary analyzed values of the compounds and the values calculated from the structural formulas of the compounds.

Example 22

The chromene compound obtained in Example 1 was mixed into a polymerizable monomer composition blended with a photopolymerization initiator in a manner as described below, and was applied onto the surface of the lens substrate and was polymerized.

TABLE 6

| Ex. No. | Found | | | | | Calculated | | | | | 1H-NMR (NMR) | |
|---|---|---|---|---|---|---|---|---|---|---|---|---|
| | C | H | N | O | others | C | H | N | O | others | | |
| 2 | 79.96 | 6.15 | | 13.89 | | 79.98 | 6.13 | | 13.90 | | δ5.6 – 9.0 | 20H |
| | | | | | | | | | | | δ1.0 – 4.0 | 22H |
| 3 | 80.40 | 6.16 | 2.01 | 11.43 | | 80.43 | 6.18 | 2.00 | 11.40 | | δ5.6 – 9.0 | 21H |
| | | | | | | | | | | | δ1.0 – 4.0 | 22H |
| 4 | 83.00 | 7.21 | 1.78 | 8.01 | | 82.98 | 7.22 | 1.76 | 8.04 | | δ5.6 – 9.0 | 20H |
| | | | | | | | | | | | δ1.0 – 4.0 | 37H |
| 5 | 82.71 | 6.24 | | 11.05 | | 82.73 | 6.25 | | 11.02 | | δ5.6 – 9.0 | 18H |
| | | | | | | | | | | | δ1.0 – 4.0 | 18H |
| 6 | 82.84 | 6.68 | 1.87 | 8.61 | | 82.78 | 6.67 | 1.89 | 8.65 | | δ5.6 – 9.0 | 21H |
| | | | | | | | | | | | δ1.0 – 4.0 | 28H |
| 7 | 80.36 | 6.53 | 1.98 | 6.67 | S: 4.48 | 80.30 | 6.60 | 1.95 | 6.69 | S: 4.47 | δ5.6 – 9.0 | 20H |
| | | | | | | | | | | | δ1.0 – 4.0 | 27H |
| 8 | 80.83 | 6.24 | 1.91 | 11.02 | | 80.85 | 6.23 | 1.92 | 10.99 | | δ5.6 – 9.0 | 21H |
| | | | | | | | | | | | δ1.0 – 4.0 | 24H |
| 9 | 84.74 | 5.78 | 1.70 | 7.78 | | 84.75 | 5.76 | 1.70 | 7.79 | | δ5.6 – 9.0 | 29H |
| | | | | | | | | | | | δ1.0 – 4.0 | 16H |
| 10 | 83.03 | 7.01 | 1.77 | 8.19 | | 82.94 | 7.09 | 1.79 | 8.18 | | δ5.6 – 9.0 | 21H |
| | | | | | | | | | | | δ1.0 – 4.0 | 34H |
| 11 | 79.50 | 6.51 | 1.78 | 12.21 | | 79.46 | 6.54 | 1.78 | 12.21 | | δ5.6 – 9.0 | 21H |
| | | | | | | | | | | | δ1.0 – 4.0 | 30H |

TABLE 7

| Ex. No. | Found | | | | | Calculated | | | | | 1H-NMR (NMR) | |
|---|---|---|---|---|---|---|---|---|---|---|---|---|
| | C | H | N | O | others | C | H | N | O | others | | |
| 12 | 83.07 | 6.58 | 1.85 | 8.50 | | 83.06 | 6.57 | 1.86 | 8.51 | | δ5.6 – 9.0 | 21H |
| | | | | | | | | | | | δ1.0 – 4.0 | 28H |
| 13 | 83.18 | 6.85 | 1.81 | 8.16 | | 83.15 | 6.85 | 1.80 | 8.20 | | δ5.6 – 9.0 | 21H |
| | | | | | | | | | | | δ1.0 – 4.0 | 32H |
| 14 | 82.38 | 6.64 | | 10.98 | | 82.39 | 6.64 | | 10.97 | | δ5.6 – 9.0 | 20H |
| | | | | | | | | | | | δ1.0 – 4.0 | 28H |
| 15 | 81.26 | 6.91 | 1.78 | 10.05 | | 81.27 | 6.95 | 1.76 | 10.02 | | δ5.6 – 9.0 | 21H |
| | | | | | | | | | | | δ1.0 – 4.0 | 24H |
| 16 | 83.05 | 6.72 | 1.85 | 8.38 | | 83.11 | 6.71 | 1.83 | 8.36 | | δ5.6 – 9.0 | 21H |
| | | | | | | | | | | | δ1.0 – 4.0 | 30H |
| 17 | 78.86 | 5.13 | 2.04 | 13.97 | | 78.81 | 5.14 | 2.04 | 14.00 | | δ5.6 – 9.0 | 21H |
| | | | | | | | | | | | δ1.0 – 4.0 | 14H |
| 18 | 82.13 | 6.54 | 2.09 | 9.24 | | 82.07 | 6.59 | 2.04 | 9.30 | | δ5.6 – 9.0 | 21H |
| | | | | | | | | | | | δ1.0 – 4.0 | 24H |
| 19 | 79.24 | 6.79 | 1.75 | 12.22 | | 79.26 | 6.78 | 1.78 | 12.18 | | δ5.6 – 9.0 | 20H |
| | | | | | | | | | | | δ1.0 – 4.0 | 23H |
| 20 | 84.65 | 6.93 | 1.92 | 6.50 | | 84.63 | 6.97 | 1.90 | 6.50 | | δ5.6 – 9.0 | 22H |
| | | | | | | | | | | | δ1.0 – 4.0 | 19H |
| 21 | 80.94 | 6.41 | 1.88 | 10.77 | | 80.94 | 6.39 | 1.89 | 10.78 | | δ5.6 – 9.0 | 20H |
| | | | | | | | | | | | δ1.0 – 4.0 | 27H |

The polymerizable monomer composition was obtained by mixing various radically polymerizable monomers according to the following recipe.

| | |
|---|---|
| 2,2-Bis(4-methacryloyloxypentaethoxyphenyl)propane: | 50 parts by mass |
| Polyethylene glycol diacrylate (average molecular weight, 532): | 10 parts by mass |
| Trimethylolpropane trimethacrylate: | 10 parts by mass |
| Polyester oligomer hexaacrylate (EB-1830, manufactured by Dycell UBC Co.): | 10 parts by mass |
| Glycidyl methacrylate: | 10 parts by mass |

One part by mass of the chromene compound obtained in Example 1 was added to 90 parts by mass of the above polymerizable monomer composition and was mixed therein to a sufficient degree, and to which were, further, added 0.5 parts by mass of a polymerization initiator, 5 parts by mass of a bis(1,2,2,6,6-pentamethyl-4-piperidyl)sebacate which is a stabilizer, 7 parts by mass of a γ-methacryloyloxypropyltrimethoxy silane which is a silane coupling agent, and 3 parts by mass of an N-methyldiethanolamine, and were mixed to a sufficient degree.

As the polymerization initiator, the CGI 1850 which is a mixture of 1-hydroxycyclohexylphenylketone and bis(2,6-dimethoxybenzoyl)-2,4,4-trimethylpentylphosphine oxide (weight ratio, 1:1) was used.

By using a spin coater, 1H-DX2, manufactured by Mikasa Co., the surface of a lens substrate (CR39: allyl plastic lens, refractive index=1.50) was spin-coated with about 2 g of the mixed solution obtained above. The surface-coated lens was irradiated with the light of a metal halide lamp of an output of 150 mW/cm² in a nitrogen gas atmosphere for 2 minutes to cure the coating layer to thereby form a thin photochromic cured film (film thickness: 40 μm).

The thus obtained photochromic lens was evaluated for its photochromic properties as described below. The results were as shown in Table 8.

(1) Maximum Absorption Wavelength (λMax):

A maximum absorption wavelength when developing a color found by using a spectrophotometer (instantaneous multi-channel photo detector, MCPD 3000) manufactured by Otsuka Denshi Kogyo Co. The maximum absorption wavelength affects the color tone of the color that is developed.

(2) Color Density {ε (120)–ε(0)}:

A difference between the absorbancy [ε (120)] at the maximum absorption wavelength after irradiated with the light for 120 seconds and the ε (0). The higher this value, the more excellent the photochromic property.

(3) Degree of Deterioration={$(A_0-A_x)/A_0$}:

The deterioration acceleration testing was conducted to evaluate the light resistance of color developed upon the irradiation with light, and the degree of deterioration was measured.

That is, the obtained sample (photochromic lens) was deteriorated for 50 hrs in an accelerated manner by using the Xenon Weather-Ometer X25 manufactured by Suga Shikenki Co. The color densities were evaluated before and after the deterioration. The color density ($A_0$) before the testing and the color density ($A_{50}$) after the testing were measured to calculate the degree of deterioration {$(A_0-A_{50})/A_0$} which was used as an index of light resistance of color that is developed. The lower the degree of deterioration, the higher the light resistance of color that develops.

Examples 23 to 42

Thin photochromic cured films were obtained in the same manner as described above but using the compounds obtained in Examples 2 to 21 as the chromene compounds, and were evaluated for their properties. The results were as shown in Table 8 and Table 9.

TABLE 8

| Example No. | Compound No. | λmax (nm) | Color density ε(120)-ε(0) | Degree of deterioration (50 hrs.) (A0-A50)/A0 × 100 |
|---|---|---|---|---|
| 22 | 1 | 442 | 0.75 | 17% |
| | | 578 | 0.92 | |
| 23 | 2 | 438 | 0.94 | 17% |
| | | 572 | 0.78 | |
| 24 | 3 | 458 | 1.23 | 15% |
| | | 580 | 0.78 | |
| 25 | 4 | 440 | 0.88 | 14% |
| | | 582 | 0.81 | |
| 26 | 5 | 444 | 0.43 | 19% |
| | | 588 | 0.56 | |
| 27 | 6 | 436 | 0.94 | 13% |
| | | 590 | 1.02 | |
| 28 | 7 | 462 | 0.64 | 16% |
| | | 591 | 0.81 | |
| 29 | 8 | 485 | 0.78 | 21% |
| | | 602 | 0.81 | |
| 30 | 9 | 487 | 0.79 | 13% |
| | | 598 | 0.84 | |
| 31 | 10 | 471 | 0.68 | 28% |
| | | 569 | 0.57 | |
| 32 | 11 | 486 | 0.65 | 18% |
| | | 594 | 0.71 | |

TABLE 9

| Example No. | Compound No. | λmax (nm) | Color density ε(120)-ε(0) | Degree of deterioration (50 hrs.) (A0-A50)/A0 × 100 |
|---|---|---|---|---|
| 33 | 12 | 475 | 0.55 | 25% |
| | | 567 | 0.53 | |
| 34 | 13 | 480 | 0.98 | 17% |
| | | 582 | 0.96 | |
| 35 | 14 | 439 | 0.82 | 26% |
| | | 565 | 0.46 | |
| 36 | 15 | 488 | 0.72 | 14% |
| | | 595 | 0.78 | |
| 37 | 16 | 470 | 0.55 | 16% |
| | | 558 | 0.43 | |
| 38 | 17 | 482 | 0.83 | 30% |
| | | 590 | 0.95 | |
| 39 | 18 | 490 | 0.74 | 11% |
| | | 602 | 0.85 | |
| 40 | 19 | 487 | 0.95 | 14% |
| | | 594 | 0.94 | |
| 41 | 20 | 481 | 0.54 | 13% |
| | | 588 | 0.67 | |
| 42 | 21 | 486 | 0.80 | 18% |
| | | 590 | 0.89 | |

Comparative Examples 1 and 2

For comparison, thin photochromic cured films were obtained in the same manner as in the above Examples but using the compounds represented by the following formulas (A) and (B), and were evaluated for their properties. The results were as shown in Table 10.

TABLE 10

(A) [Structure: H3CO-substituted chromene with N(CH3)2, OCH3, OCH3 groups]

(B) [Structure: chromene with N(CH3)2, OCH3, phenyl groups]

| Example No. | Compound No. | λmax (nm) | Color density ϵ(120) − ϵ(0) | Degree of deterioration (50 hrs.) (A0-A50)/A0 × 100 |
|---|---|---|---|---|
| 1 | A | 490 | 0.28 | 68% |
|   |   | 600 | 0.29 |   |
| 2 | B | 486 | 0.16 | 72% |
|   |   | 588 | 0.17 |   |

When the comparative compounds (A) and (B) were used, defective polymerization took place at the time of curing the coatings, and thin and evenly cured films could not be obtained. These compounds having hydrogen at the benzyl position are not stable against the radicals. It is, therefore, considered that the radicals generated at the time of photopolymerization are partly consumed by the reaction (decomposition) with these compounds, and the radicals were not sufficiently available for the polymerization.

The chromene compounds of the invention shown in Examples 1 to 21 have lower degrees of deterioration and higher recurring resistances of photochromic properties than those of the compounds of Comparative Example 1 and Comparative Example 2. Besides, the chromene compounds of the present invention have high color densities per a unit amount. Therefore, the photochromic plastic lenses produced by using the chromene compounds of the invention exhibit excellent photochromic properties.

Examples 43, Comparative Examples 3 and 4

Next, the photochromic cured bodies obtained by the in-mass method were evaluated as described below. That is, the components of the following recipe were mixed together to a sufficient degree to prepare a photochromic curable composition.

Photochromic Curable Composition:

| | |
|---|---|
| Chromeme compound obtained in Example 1: | 0.04 parts by mass |
| Tetraethylene glycol dimethacrylate: | 13 parts by mass |
| 2,2-Bis[4-(methacryloxyethoxy)phenyl]propane: | 48 parts by mass |
| Polyethylene glycol monoallyl ether: | 2 parts by mass |
| Trimethylolpropane trimethacrylate: | 20 parts by mass |
| Glycidyl methacrylate: | 9 parts by mass |
| t-Butylperoxy 2-ethyl hexanoate (polymerization initiator: | 1 part by mass |

Next, the obtained composition was cast into a mold constituted by a glass plate and a gasket made from an ethylene/vinyl acetate copolymer, and was cast-polymerized. The polymerization was conducted by using an air furnace, gradually elevating the temperature from 30° C. to 90° C. over a period of 18 hours, and holding the temperature at 90° C. for 2 hours. After the polymerization, the cured body was taken out from the mold, i.e., from the glass mold. The obtained cured body (sample having a thickness of 2 mm) was evaluated for its photochromic properties according to the same method as described above.

For comparison, further, photochromic polymers were obtained in the same manner by using the compound (Comparative Example 3) represented by the formula (A) and the compound (Comparative Example 4) represented by the formula (B) instead of using the chromene compound of Example 1, and were evaluated for their properties. The results were as shown in Table 11.

TABLE 11

| | Compound No. | λmax (nm) | Color density ϵ(120)-ϵ(0) |
|---|---|---|---|
| Example 43 | 1 | 443 | 1.11 |
|   |   | 572 | 1.32 |
| Comparative Example 3 | A | 498 | 0.81 |
|   |   | 596 | 0.80 |
| Comparative Example 4 | B | 488 | 0.68 |
|   |   | 590 | 0.79 |

It will be learned that the photochromic cured body (high molecular molded body) obtained by the in-mass method in Example 43 by using the chromene compound of the invention exhibits excellent color density per the unit weight like the photochromic cured body obtained by the coating method.

The invention claimed is:

1. A chromene compound represented by the following formula (1), (1)

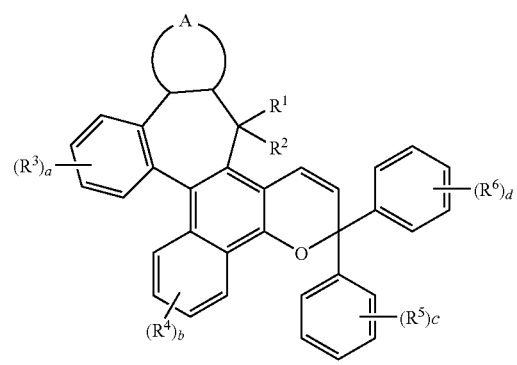

wherein,

"A" is an annulated ring,

R¹ and R² are, respectively, hydrogen atoms, hydroxyl groups, alkyl groups, cycloalkyl groups, alkoxy groups, aralkyl groups, aralkoxy groups or aryl groups, R¹ and R² may be linked to each other to form a ring, and R¹ and R² together may form a carbonyl group with a carbon atom to which these groups are bonded, R³, R⁴, R⁵ and R⁶ are, respectively, hydroxyl groups, alkyl groups, cycloalkyl groups, alkoxy groups, aralkyl groups, aralkoxy groups, aryl groups, amino groups, cyano groups, nitro groups, halogen atoms, halogenoalkyl groups, halogenoalkoxy groups, or heterocyclic groups having a nitrogen atom as a hetero atom and being bonded through a bond at the nitrogen atom as a bonding hand and, when R³s are present in a plural number, two R³s may be coupled together to form a ring, "a" and "b" are, respectively, integers of 0 to 4, and "c" and "d" are, respectively, integers of 0 to 5.

2. The chromene compound according to claim 1 represented by the following formula (2),

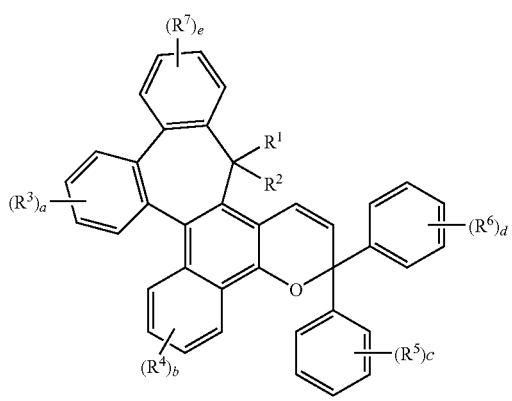

(2)

wherein,

R¹, R², R³, R⁴, R⁵, R⁶, "a", "b", "c" and "d" are as defined in the above formula (1), R⁷ is a hydroxyl group, alkyl group, cycloalkyl group, alkoxy group, aralkyl group, aralkoxy group, aryl group, amino group, cyano group, nitro group, halogen atom, halogenoalkyl group, halogenoalkoxy group or a heterocyclic group having a nitrogen atom as a hetero atom and being bonded through a bond at the nitrogen atom as a bonding hand, and "e" is an integer of 0 to 4.

3. The chromene compound according to claim 2 represented by the following formula (3),

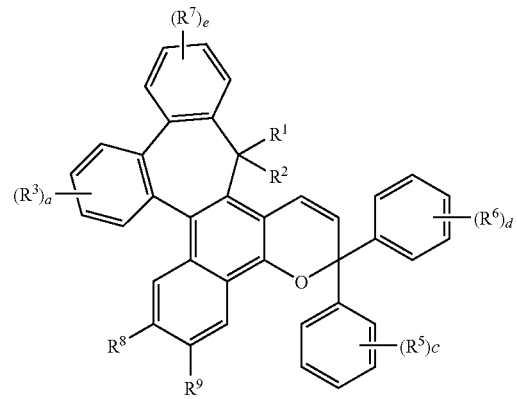

(3)

wherein,

R¹, R², R³, R⁴, R⁵, R⁶, "a", "b", "c" and "d" are as defined in the above formula (1), R⁷ and "e" are as defined in the above formula (2), R⁸ and R⁹ are, respectively, hydroxyl groups, alkyl groups, cycloalkyl groups, alkoxy groups, aralkyl groups, aralkoxy groups, aryl groups, amino groups, cyano groups, nitro groups, halogen atoms, halogenoalkyl groups, halogenoalkoxy groups or heterocyclic groups having a nitrogen atom as a hetero atom and are bonded with said nitrogen atom as a bonding hand, and R⁸ and R⁹ together may form a ring, and said ring formed by R⁸ and R⁹ have elements in a number of 5 to 7, and said ring may include one or two oxygen atoms, nitrogen atoms or sulfur atoms as hetero atoms.

4. A photochromic curable composition containing the chromene compound of claim 1 and a polymerizable monomer.

5. A photochromic optical article comprising a high molecular molded body in which the chromene compound of claim 1 is dispersed.

6. An optical article comprising an optical substrate having a surface which is at least partly coated with a high molecular film, said high molecular film having the chromene compound of claim 1 dispersed therein.

* * * * *